United States Patent [19]
Royalty et al.

[11] Patent Number: 5,707,934
[45] Date of Patent: *Jan. 13, 1998

[54] PLANT GROWTH REGULATION USING 3-CYANO-1-PHENYLPYRAZOLES SUCH AS FIPRONIL

[75] Inventors: Reed Nathan Royalty, Raleigh, N.C.; Nguyen Dang Long, Hochiminville, Viet Nam; Michael Thomas Pilato; Nicholas Mark Hamon, both of Cary, N.C.; Ngadi Yahmad, Jember; Djoko Prabowo Sastrosatomo, Jakarta, both of Indonesia

[73] Assignee: Rhone-Poulenc Inc., Research Triangle Park, N.C.

[*] Notice: The term of this patent shall not extend beyond the expiration date of Pat. No. 5,585,329.

[21] Appl. No.: 622,628

[22] Filed: Mar. 27, 1996

Related U.S. Application Data

[63] Continuation-in-part of Ser. No. 593,418, Jan. 29, 1996, abandoned, which is a continuation-in-part of Ser. No. 430,499, Apr. 28, 1995, Pat. No. 5,585,329.

[51] Int. Cl.$^6$ ............... A01N 43/40; A01N 43/56
[52] U.S. Cl. ............... 504/253; 504/280; 504/282
[58] Field of Search .................. 504/280, 282, 504/253

[56] References Cited

U.S. PATENT DOCUMENTS

| | | | |
|---|---|---|---|
| 4,614,533 | 9/1986 | Schallner et al. | 71/92 |
| 4,614,534 | 9/1986 | Stetter et al. | 71/92 |
| 4,787,930 | 11/1988 | Gehring et al. | 71/92 |
| 4,946,492 | 8/1990 | Pissiotas et al. | 71/72 |
| 5,039,329 | 8/1991 | Pissiotas et al. | 71/72 |
| 5,232,940 | 8/1993 | Hatton et al. | 514/407 |
| 5,236,938 | 8/1993 | Huang et al. | 514/341 |
| 5,306,694 | 4/1994 | Phillips et al. | 504/253 |
| 5,547,974 | 8/1996 | Hatton et al. | 514/406 |

FOREIGN PATENT DOCUMENTS

| | | |
|---|---|---|
| 0167028 | 1/1986 | European Pat. Off. |
| 0235558 | 9/1987 | European Pat. Off. |
| 0295117 | 12/1988 | European Pat. Off. |
| 0347382 | 12/1989 | European Pat. Off. |
| 0385809 | 9/1990 | European Pat. Off. |
| 0403300 | 12/1990 | European Pat. Off. |
| 0500209 | 8/1992 | European Pat. Off. |
| 0679650 | 11/1995 | European Pat. Off. |
| 2696904 | 4/1994 | France . |
| 19511269 | 10/1995 | Germany . |
| 87/03781 | 7/1987 | WIPO . |
| 93/06089 | 4/1993 | WIPO . |
| 94/21606 | 9/1994 | WIPO . |

OTHER PUBLICATIONS

Database WPI/Derwent, abstract No. 88–240111, published 1988; also Chemical Abstracts, vol. 110, abstract No. 90608 and Patent Abstracts of Japan, vol. 12, No. 450 (C–547), published Nov. 25, 1988; all abstracts of JP 63 174905 published Jul. 19, 1988 (Shozo et al).

Chemical Abstracts, vol. 107, No. 19, Nov. 9, 1987 abstarct No. 176028; also Patent Abstracts of Japan, vol. 11, No. 369 (C–461), published Dec. 2, 1987 and Database WPI/Derwent, abstract No. 87–210794, published 1987 (all abstracts of JP 62 138475 published Jun. 22, 1987 of Shozo et al).

*Agrow World Crop Protection News*, No. 244, Nov. 17, 1995, p. 8.

*Arthropod Management Tests*, vol. 20, report No. 99F, p. 225, Entomological Society of America, Special Publication, published no earlier than Jul. 10, 1995 (Bernhardt).

*Arthropod Management Tests*, vol. 20, report No. 100F, pp. 225–226, Entomological Society of America, Special Publication, published no earlier than Jul. 10, 1995 (Bernhardt).

*Arthropod Management Tests*, vol. 20, report No. 101F, p. 226, Entomological Society of America, Special Publication, published no earlier than Jul. 10, 1995 (Bernhardt).

*Arthropod Management Tests*, vol. 20, report No. 103F, pp. 227–228, Entomological Society of America, Special Publication, published no earlier than Jul. 10, 1995 (Palrang et al).

*Arthropod Management Tests*, vol. 20, report No. 104F, pp. 228, Entomological Society of America, Special Publication, published no earlier than Jul. 10, 1995 (Way et al).

*Primary Examiner*—S. Mark Clardy
*Attorney, Agent, or Firm*—Burns, Doane, Swecker & Mathis, L.L.P.

[57] ABSTRACT

This invention relates to a new method of plant growth regulation whereby a 1-phenylpyrazole such as fipronil is applied to a crop or a seed.

31 Claims, No Drawings

PLANT GROWTH REGULATION USING 3-CYANO-1-PHENYLPYRAZOLES SUCH AS FIPRONIL

CROSS-REFERENCE TO RELATED APPLICATIONS

This is a continuation-in-part of prior U.S. patent application Ser. No. 08/593,418, filed Jan. 29, 1996, now abandoned which is a continuation-in-part of prior U.S. patent application Ser. No. 08/430,499, filed Apr. 28, 1995, now U.S. Pat. No. 5,585,329 said applications being incorporated by reference herein in their entireties and relied upon.

The present invention relates to a new method for treatment of plants to induce growth regulating responses.

The term "method for regulating plant growth" or the term "growth regulation process" or the use of the words "growth regulation" or other terms using the word "regulate" as used in the instant specification relate to a variety of plant responses which attempt to improve some characteristic of the plant as distinguished from pesticidal action, the intention of which is to destroy or stunt the growth of a plant or a living being. For this reason the compounds used in the practice of this invention are used in amounts which are non-phytotoxic with respect to the plant being treated. Plant growth regulation is a desirable way to improve plants and cropping so as to obtain better plants and better conditions of agriculture practice.

The present invention provides a method for regulating the growth of plants comprising applying to said plants, to the seeds from which they grow or to the locus in which they grow, a non-phytotoxic, effective plant growth regulating amount of a compound having the formula:

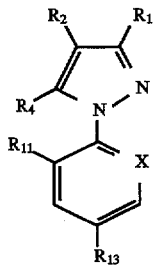

(I)

wherein:

$R_1$ is CN or methyl;

$R_2$ is $S(O)_n R_3$;

$R_3$ is alkyl or haloalkyl;

$R_4$ is selected from the group comprising a hydrogen atom, a halogen atom, and a radical which may be $-NR_5R_6$, $C(O)OR_7$, $-S(O)_m R_7$, alkyl, haloalkyl, $-OR_8$, or $-N=C(R_9)(R_{10})$; $R_4$ is preferably a amino group, which is unsubstituted or which bears one or two substituents selected from the group consisting of alkyl, haloalkyl, acyl and alkoxycarbonyl;

$R_5$ and $R_6$ are independently selected from a hydrogen atom, alkyl, haloalkyl, $-C(O)$alkyl, $-S(O)_r CF_3$; or $R_5$ and $R_6$ form together a divalent radical which may be interrupted by one or more heteroatoms;

$R_7$ is selected from alkyl or haloalkyl;

$R_8$ is selected from alkyl, haloalkyl or the hydrogen atom;

$R_9$ is selected from the hydrogen atom and alkyl;

$R_{10}$ selected from phenyl or heteroaryl that is optionally substituted by one or more hydroxy, a halogen atom, $-O$-alkyl, $-S$-alkyl, cyano, or alkyl or combinations thereof;

X is selected from the Nitrogen atom and the radical $C-R_{12}$;

$R_{11}$ and $R_{12}$ are independently selected from a halogen atom or the hydrogen atom;

$R_{13}$ is selected from a halogen atom, haloalkyl, haloalkoxy, $-S(O)_q CF_3$, $-SF_5$, preferably from a halogen atom, haloalkyl, haloalkoxy, $-SF_5$;

m,n,q,r are independently selected from 0, 1, and 2;

provided that when $R_1$ is methyl, $R_3$ is haloalkyl, $R_4$ is $NH_2$, $R_{11}$ is Cl, $R_{13}$ is $CF_3$, and X is N.

The alkyl and alkoxy groups of the formula (I) are preferably lower alkyl and alkoxy groups, that is, radicals having one to four carbon atoms. The haloalkyl and haloalkoxy groups likewise preferably have one to four carbon atoms. The haloalkyl and haloalkoxy groups can bear one or more halogen atoms; preferred groups of this type include $-CF_3$ and $-OCF_3$.

A preferred group of plant growth regulating 1-phenylpyrazoles for use in the present invention are those of formula (I) wherein:

$R_1$ is CN; and/or $R_4$ is $-NR_5R_6$; and/or $R_5$ and $R_6$ are independently selected from the hydrogen atom, alkyl, haloalkyl, $-C(O)$alkyl, $C(O)OR_7$; and/or X is $C-R_{12}$; and/or $R_{13}$ is selected from a halogen atom, haloalkyl, haloalkoxy, or $-SF_5$.

A particularly preferred group of plant growth regulating 1-phenylpyrazoles for use in the present invention are those of formula (I) wherein:

$R_1$ is CN;

$R_4$ is $-NR_5R_6$;

$R_5$ and $R_6$ are independently selected from the hydrogen atom, alkyl, haloalkyl, $-C(O)$alkyl, $C(O)OR_7$;

X is $C-R_{12}$;

$R_{13}$ is selected from a halogen atom, haloalkyl, haloalkoxy, or $-SF_5$.

Specific pyrazole derivatives usable in the method for regulating plant growth falling within the scope of the present invention include 5-amino-3-cyano-1-(2,6-dichloro-4-trifluoromethylphenyl)-4-trifluoromethylsulfinylpyrazole. This especially preferred plant growth regulator for use in the present invention is hereafter called compound A.

According another feature of the instant invention, there is provided a method of regulating the growth of a plant at a locus at which there are no insects, or at which they are not expected to be or through which they are not expected to pass, or traverse, or inhabit or visit or fly, said method comprising the application thereto or to the plant seed therefrom of a non-phytotoxic, effective plant growth regulating amount of a compound of formula (I).

Another aspect of the invention is method for regulating the growth of plants selected from the group consisting of rice, corn, cereal, vegetable and soybean plants and turf, said method comprising applying to said plants, to the seeds from which they grow or to the locus in which they grow, a non-phytotoxic, effective plant growth regulating amount of a compound of formula (I).

Another aspect of the invention is a method for regulating the growth of soybean plants comprising applying to the seeds from which said soybean plants grow, prior to sowing said seeds, a non-phytotoxic, effective plant growth regulating amount of a compound of formula (I).

Another aspect of the invention is a method for treating plants in need of growth regulation, comprising applying to said plants, to the seeds from which they grow or to the locus in which they grow, a non-phytotoxic, effective plant growth regulating amount of a compound having the formula (I). This need of growth regulation is particularly great when the plants or seeds therefrom are weak or feeble or stressed or are not in growing conditions favorable to the growth of plants.

The preparation of compounds of formula (I) can be effected according to any process described in International Patent Publications No. WO 87/03781, WO 93/06089 and WO 94/21606, as well as in European Patent Publication numbers 0295117, 0403300, 0385809, and 0679650, German Patent Publication 19511269 and U.S. Pat. Nos. 5,232,940 and 5,236,938.

The 1-phenylpyrazoles of formula (I) used in the method of the present invention fall within a broader group of compounds which has been previously described as insecticides. It has been found that, surprisingly, the compounds of formula (I) and most especially compound (A), display a wide variety of plant growth regulating properties, depending upon the concentration used, the formulation employed and the type of plant species treated.

By virtue of the practice of the present invention a wide variety of plant growth responses, including the following, may be induced:

a. more developed root system
b. tillering increase
c. increase in plant height
d. bigger leaf blade
e. less dead basal leaves
f. stronger tillers
g. greener leaf color
h. less fertilizers needed
i. less seeds needed
j. more productive tillers
k. less third non productive tillers
l. earlier flowering
m. early grain maturity
n. less plant verse (lodging)
o. longer panicles
p. increased shooth growth
q. improved plant vigour
r. early germination
s. more fruit and better yield (weight) of fruit.

It is intended that as used in the instant specification the term "method for regulating plant growth" or "method for regulating the growth of plants" means the achievement of any of the aforementioned nineteen categories of response or any other modification of plant, seed, fruit or vegetable (whether the fruit or vegetable is unharvested or harvested) so long as the net result is to increase growth or benefit any property of the plant, seed, fruit or vegetable as distinguished from any pesticidal action (unless the present invention is practised in conjunction with or in the presence of a pesticide, for example a herbicide). The term "fruit" as used in the instant specification is to be understood as meaning anything of economic value that is produced by the plant.

Suitable formulations for plant growth regulating compositions are known. A description of suitable formulations which may be used in the method of the invention can be found in international patent publications WO 87/3781, 93/6089, 94/21606 as well as in European patent application 295117 and U.S. Pat. No. 5232940. The formulations described in said prior art are mainly intended for insecticidal purposes. Formulations or compositions for plant growth regulating uses can be made in a similar way, adapting the ingredients, if necessary, to make them more suitable to the plant or soil to which the application is to be made.

The 1-phenylpyrazoles of formula (I) may be applied for plant growth regulating purposes to the foliage of plants and/or to the soil in which said plants are growing. Applications to the soil are often in the form of granules which are usually applied in sufficient amount to provide a rate of from about 0.005 kg/ha to about 0.5 kg/ha of active ingredient, preferably between 0.01 and 0.2 kg/ha.

A preferred embodiment of the invention is a method for regulating the growth of plants comprising applying to the seeds from which said plants grow, prior to sowing said seeds, a non-phytotoxic, effective plant growth regulating amount of a compound having the formula (I). The seed may be treated, especially by coating or embedding or impregnation or soaking or dipping in liquid or paste formulations which are known per se and are subsequently dried. Seed comprising 2 to 1000 gram per quintal of a compound of formula (I), preferably 5 to 800 g/q, most preferably 5 to 250 g/q are particularly appropriate for this purpose.

Advantageously, compounds of formula (I) can also be formulated as flowable compositions, wettable powders, microemulsions and the like, all of which lend themselves to soil, water and/or foliage application and provide the requisite plant growth regulating action. Such formulations include the compounds of the invention admixed with inert, agriculturally acceptable solid or liquid diluents.

The formulations may comprise other active ingredients in addition to the compound of formula (I). For example, mixtures with fungicidally active ingredient may be used.

Wettable powders and granular concentrate formulations for use in the method of the invention can be prepared by grinding together a 1-phenylpyrazole compound of formula (I), with about 1% to 20% by weight of a solid anionic surfactant. One suitable anionic surfactant is a dioctyl ester of sodium sulfosuccinic acid. About 85% to 95%, by weight, of an inert solid diluent, such as montmorillonite, attapulgite, chalk, talc, kaolin, diatomaceous earth, limestone, silicates or the like is also included in such formulations, as well as other adjuvants as previously indicated.

In addition to the granules and wettable powder formulations described hereinabove, flowable formulations can be used since they are readily dispersible in water and can be applied to the proper locus where the plant growth regulating action is required.

The pyrazole derivatives used in the method of the present invention have a low solubility in water but can be used at low doses. So, they can be applied to plants in aqueous solutions or emulsions or, preferably, suspensions comprising water and, optionnally, other adjuvants. Partial aqueous media include those formed of water and, for instance, acetone or methyl ethyl ketone. Any liquid medium can be used provided that it is not toxic to the plant, and preferably not to the environment. Where any particular pyrazole derivative is less water-soluble, it can be solubilized by the use of co-solvents or wetting agents or it can be suspended by mean of dispersing agents which can be used simultaneously with e.g. surfactants and extenders. Other media, including solids, like talc, will occur to those skilled in the art. The compounds used in the process of this invention can be absorbed onto solid carriers such as vermiculite, attaclay, talc and the like for application via a granular vehicle. Application of diluted aqueous formulations or solids is accomplished using conventional equipment that is well known in the art.

As will be demonstrated in connection with certain examples in this specification, compounds used in the process of the present invention have been effective in regulating plant growth and development in connection with a wide variety of plant species at various concentrations of active pyrazole compounds.

The precise amount of pyrazole compound to be used will depend, inter alia, upon the particular plant species being treated. A suitable dose may be determined by the man skilled in the art by routine experimentation. The plant response will depend upon the total amount of compound used, as well as the particular plant species which is being treated. Of course, the amount of pyrazole compound should be non-phytotoxic with respect to the plant being treated. Although the preferred method of application of the compounds used in the process of this invention is directly to the foliage and stems of plants, the compounds can be applied to the soil in which the plants are growing. Such compounds will be root-absorbed to a sufficient extent so as to result in plant responses in accordance with the teachings of this invention.

The process of the present invention is often preferably carried out on growing plants as set forth in many of the examples in this specification. However, the process of the present inventions is advantageously carried out as a seed treatment, for instance, of rice seed, lettuce seeds, oat seeds and soybean seeds.

The following examples are illustrative of methods of plant growth regulation according to the invention, but should not be understood as limiting the invention as modifications in materials and methods will be apparent to the skilled worker. All measurements of plant growth regulating effects were determined using untreated seeds and/or plants as controls.

EXAMPLE 1

Rice seed was treated by mixing the seed with a suspension concentrate containing 5% w/w of compound A. This mixing resulted in a coated seed which was immediately sown on a 1000 m2 area so as to have 30g/ha of active ingredient. The results were observed from the seedling emergence through to harvest. Some insects were present and killed. Results were observed 35 days after sowing. A 5.4% yield increase was observed with following plant growth regulating effect: greener plants, higher plants, less dead basal leaves, bigger leaf blade, flowering 2 days earlier.

EXAMPLE 2

Example 1 was repeated. Results were observed 60 days after sowing. A 7% yield increase was observed with following plant growth regulating effect: greener plants, higher plants, less dead basal leaves, bigger leaf blade, flowering 2 days earlier, longer panicles, brighter color of grain.

EXAMPLE 3

Example 1 was repeated except that 40 g/ha of active ingredient were applied. The same results were obtained but also stronger tillers were observed as well as less plant verse.

EXAMPLE 4

Example 1 was repeated except that 50 g/ha of active ingredient were applied. The same results were obtained but also a 15% growth tillers increase was observed as well as a 9.5% yield increase.

EXAMPLE 5

Rice seed was sown and the seed bed (acid sulphate soil) was treated (soil treatment) by spraying it with a suspension concentrate containing 5% w/w of compound A. After treatment, transplantation of rice was made as usual. The treatment of seed bed was made 24 days before transplantation. The following plant growth regulating effects were observed: stronger seedlings, flowering 6 days earlier, 25% increase in tillers, harvest 6 days earlier, 100% yield increase.

EXAMPLE 6

Rice seed was sown and the flooded seed bed was treated (soil treatment) by sprinkling granules containing 0.3% w/w of compound A on it. After treatment, transplantation of rice was made as usual. The treatment of seed bed was made 11 days before transplantation. The following plant growth regulating effects were observed: stronger seedlings, 50% increase in tillers, fertilizers reduced by 40 kg urea and 50 kg/ha of superphosphate, 7% yield increase.

EXAMPLE 7

Corn seeds were sown in 3.5 liters pots (six plants per pot). Immediately after sowing, granules containing compound A were spread on the soil. The granules contained 1.5% w/w of active ingredient and they were spread so as to have a dose of 120 g/ha of active ingredient on the soil. Plants were properly watered. One month and one week after, the dry root weight was measured. The root weight is about 42 g for the treated pots and 30 g for the untreated pots.

EXAMPLE 8

Rice seed was germinated 48 hours in water at 30° C. and then sown in pots. After the emergence of the seedings, granules containing 0.3% w/w of compound A were applied to the soil at rates of 200 and 100 g/ha. No phytotoxicity was observed with any of the formulations or rates. Periodically, sets of pots were harvested and dry weights of the roots were determined. Pyrazole treatments increased the dry root mass per pot by an average of 36% over that of the untreated seedlings 28 days after treatment.

EXAMPLE 9

Soybean seed was treated with a mixture of an insecticidally active compound together with a fungicidally active compound. Soybean was sown at 60 kg/ha in a plot having, after growing, 1000 plants per plot. The seeds germinated and the plants were grown up, up to the time of harvest, and observations were made all along that time.

The results in the following Table demonstrate clearly that the plant growth regulating activity of compound A is not attributable simply to its insecticidal activity. Other comparable insecticides do not produce plant growth regulation whereas the results obtained with compound A clearly show a plant growth regulatory effect.

The following active ingredients and doses were applied:

| Insecticide | Fungicide | Dose of insecticide in g/ha | Dose of fungicide in g/ha | Yield (kg) per 250 plants | Number of pod per plants (average) |
| --- | --- | --- | --- | --- | --- |
| Compound A | Benomyl | 30 | 150 | 4.87 | 26 |
| Compound A | Captan | 30 | 300 | 6.21 | 26.7 |
| Carbosulfan | Benomyl | 300 | 150 | 3.46 | 19.6 |
| Carbosulfan | Captan | 300 | 300 | 2.18 | 16.8 |
| Thiodicarb | Benomyl | 675 | 150 | 3.27 | 16.5 |
| Thiodicarb | Captan | 675 | 300 | 2.15 | 21.1 |
| Methomyl | Benomyl | 225 | 150 | 1.85 | 16.2 |
| Methomyl | Captan | 225 | 300 | 3.57 | 22.7 |

The following observations were made: Bean fly control was higher than 95% both with compound A and Carbosulfan. The plant growth with compound A was very much accelerated during the first month after sowing. Compound A-treated plants were taller and healthier, leaves were wider, greener and shiny, branches were stronger and there were more branches, and plant canopying was faster than other treatments so that there were less weeds.

The number of pod/plant was 24 to 37% higher with Compound A than with Carbosulfan. The yield was much higher when compound A was applied. Both the yield and the average number of pods per plant were also higher using compound A than when thiodicarb and methomyl were used.

EXAMPLE 10

Rice seed was treated with a formulation of compound A at a rate of 40 g/hectare field-sown at a rate of 150 kg/hectare and covered with a thin layer of soil. Afterwards the seed was allowed to germinate and the plants grow to maturity and the rice crop harvested. A yield increase of 660 kg/hectare above normal conditions (not sown seed treated with compound A) was found. The amount of savings in fertiliser was the following: Nitrogen—18 kg/hectare that is to say 18% less than standard protocol; Phosphates 7 kg/hectare, that is to say 16% less than standard protocol.

When repeating the experimental conditions of examples 1 to 10 with loci in which no insects were expected to be or to pass through, inhabit, visit or fly through, the same results were obtained: the plant growth regulation effects of compound A were the same as the conditions in which insects were present at the loci. The insects, if any, were eliminated by application of compound A. When no insects were expected, there is no reason to apply compound A as an insecticidally active ingredient or composition. The application of compound A for plant growth regulation purposes was producing the effects as indicated in examples 1 to 10.

While the invention has been described in terms of various preferred embodiments, the skilled artisan will appreciate that various modifications, substitutions, omissions and changes can be made without departing from the spirit thereof. Accordingly, it is intended that the scope of the present invention be limited solely by the scope of the following claims, including equivalents thereof.

What is claimed is:

1. A method for treating plants in need of plant growth promotion which are not in need of insect control, said method comprising applying to said plants, to the seeds from which they grow or to the locus in which they grow, a non-phytotoxic, effective plant growth promoting amount of a compound having the formula:

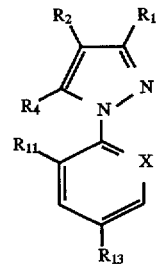

wherein:
$R_1$ is CN;
$R_2$ is $S(O)_n R_3$;
$R_3$ is alkyl or haloalkyl;
$R_4$ is —$NR_5 R_6$;
$R_5$ and $R_6$ are independently selected from the group consisting of hydrogen, alkyl, haloalkyl, C(O)alkyl and C(O)OR$_7$;
$R_7$ is alkyl;
X is C-$R_{12}$;
$R_{11}$ and $R_{12}$ are independently halogen or hydrogen;
$R_{13}$ is halogen, haloalkyl, haloalkoxy or SF$_5$; and
n is 0, 1 or 2;
said plants, seeds and locus having substantially no insects present or expected in their vicinity during plant growth.

2. A method according to claim 1, wherein the plant growth promoting amount of the compound of formula (I) applied is sufficient to provide at least one plant growth promoting effect selected from the group consisting of: (a) a more developed root system; (b) a tillering increase; (c) an increase in plant height; (d) a larger leaf blade; (e) fewer dead basal leaves; (f) stronger tillers; (g) a greener leaf color; (h) a need for less fertilizer; (i) a need for fewer seeds; (j) more productive tillers; (k) fewer nonproductive third tillers; (l) earlier flowering; (m) earlier grain maturity; (n) less plant verse; (o) longer panicles; (p) increased shoot growth; (q) improved plant vigor; (r) earlier germination; and (s) more fruit and better weight of fruit.

3. A method according to claim 2, wherein the compound of formula (I) is 5-amino-3-cyano-1-(2,6-dichloro-4-trifluoromethylphenyl)-4-trifluoromethylsulfinylpyrazole.

4. A method according to claim 2, wherein said plants are selected from the group consisting of rice, corn, cereal, vegetable and soybean plants and turf.

5. A method according to claim 4, wherein the compound of formula (I) is 5-amino-3-cyano-1-(2,6-dichloro-4-trifluoromethylphenyl)-4-trifluoromethylsulfinylpyrazole.

6. A method according to claim 1, wherein the plant growth promoting amount of the compound of formula (I) is sufficient to reduce the fertilizer requirements of said plants.

7. A method according to claim 6, wherein the compound of formula (I) is 5-amino-3-cyano-1-(2,6-dichloro-4-trifluoromethylphenyl)-4-trifluoromethylsulfinylpyrazole.

8. A method according to claim 6, wherein said plants are selected from the group consisting of rice, corn, cereal, vegetable and soybean plants and turf.

9. A method according to claim 8, wherein the compound of formula (I) is 5-amino-3-cyano-1-(2,6-dichloro-4-trifluoromethylphenyl)-4-trifluoromethylsulfinylpyrazole.

10. A method according to claim 1, wherein said plants are selected from the group consisting of rice, corn, cereal, vegetable and soybean plants and turf.

11. A method according to claim 10, wherein the compound of formula (I) is 5-amino-3-cyano-1-(2,6-dichloro-4-trifluoromethylphenyl-4-trifluoromethylsulfinylpyrazole.

12. A method according to claim 1, wherein the compound of formula (I) is 5-amino-3-cyano-1-(2,6-dichloro-4-trifluoromethylphenyl)-4-trifluoromethylsulfinylpyrazole.

13. A method according to claim 1, wherein the compound of formula (I) is applied to said plants or to the locus in which they grow in the form of granules at an application rate of from about 0.005 kg/ha to about 0.5 kg/ha of compound of formula (I).

14. A method according to claim 13, wherein the application rate is from about 0.01 kg/ha to about 0.2 kg/ha of compound of formula (I).

15. A method according to claim 1, wherein the compound of formula (I) is applied to said seeds at a dose rate of from about 2 to about 1000 grams per quintal of seed.

16. A method according to claim 15, wherein the application rate is from about 5 to about 800 grams per quintal of seed.

17. A method according to claim 16, wherein the application rate is from about 5 to about 250 grams per quintal of seed.

18. A method for treating soybean plants in need of growth promotion, said method comprising applying to the seeds from which said soybean plants grow, prior to sowing said seeds, a non-phytotoxic, effective plant growth promoting amount of a compound having the formula:

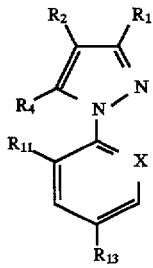

wherein:
$R_1$ is CN;
$R_2$ is $S(O)_nR_3$;
$R_3$ is alkyl or haloalkyl;
$R_4$ is $-NR_5R_6$;
$R_5$ and $R_6$ are independently selected from the group consisting of hydrogen, alkyl, haloalkyl, C(O)alkyl and C(O)OR$_7$;
$R_7$ is alkyl;
X is C-R$_{12}$;
$R_{11}$ and $R_{12}$ are independently halogen or hydrogen;
$R_{13}$ is halogen, haloalkyl, haloalkoxy or SF$_5$; and
n is 0, 1 or 2.

19. A method according to claim 18, wherein the compound of formula (I) is 5-amino-3-cyano-1-(2,6-dichloro-4-trifluoromethylphenyl)-4-trifluoromethylsulfinylpyrazole.

20. A method according to claim 18, wherein the plant growth promoting amount of the compound of formula (I) applied is sufficient to provide at least one plant growth promoting effect selected from the group consisting of: (a) a more developed root system; (b) an increase in plant height; (c) a larger leaf blade; (d) a greener leaf color; (e) a need for less fertilizer; (f) a need for fewer seeds; (g) earlier flowering; (h) increased shoot growth; (i) improved plant vigor; (j) earlier germination; and (k) more fruit and better weight of fruit.

21. A method according to claim 20, wherein the compound of formula (I) is 5-amino-3-cyano-1-(2,6-dichloro-4-trifluoromethylphenyl)-4-trifluoromethylsulfinylpyrazole.

22. A method according to claim 18, wherein the compound of formula (I) is applied to said seeds at a dose rate of from about 2 to about 1000 grams per quintal of seed.

23. A method according to claim 22, wherein the application rate is from about 5 to about 800 grams per quintal of seed.

24. A method according to claim 23, wherein the application rate is from about 5 to about 250 grams per quintal of seed.

25. A method for treating soybean plants in need of growth promotion which are not in need of insect control, said method comprising applying to the seeds from which said soybean plants grow, prior to sowing said seeds, a non-phytotoxic, effective plant growth promoting amount of a compound having the formula:

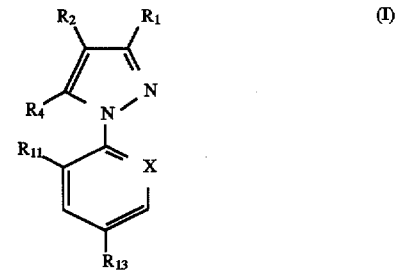

wherein:
$R_1$ is CN;
$R_2$ is $S(O)_nR_3$;
$R_3$ is alkyl or haloalkyl;
$R_4$ is $-NR_5R_6$;
$R_5$ and $R_6$ are independently selected from the group consisting of hydrogen, alkyl, haloalkyl, C(O)alkyl and C(O)OR$_7$;
$R_7$ is alkyl;
X is C-R$_{12}$;
$R_{11}$ and $R_{12}$ are independently halogen or hydrogen;
$R_{13}$ is halogen, haloalkyl, haloalkoxy or SF$_5$; and
n is 0, 1 or 2;
said plants and seeds having substantially no insects present or expected in their vicinity during plant growth.

26. A method according to claim 25, wherein the compound of formula (I) is 5-amino-3-cyano-1-(2,6-dichloro-4-trifluoromethylphenyl)-4-trifluoromethylsulfinylpyrazole.

27. A method according to claim 25, wherein the plant growth promoting amount of the compound of formula (I) applied is sufficient to provide at least one plant growth promoting effect selected from the group consisting of: (a) a more developed root system; (b) an increase in plant height; (c) a larger leaf blade; (d) a greener leaf color; (e) a need for less fertilizer; (f) a need for fewer seeds; (g) earlier flowering; (h) increased shoot growth; (i) improved plant vigor; (j) earlier germination; and (k) more fruit and better weight of fruit.

28. A method according to claim 27, wherein the compound of formula (I) is 5-amino-3-cyano-1-(2,6-dichloro-4-trifluoromethylphenyl)-4-trifluoromethylsulfinylpyrazole.

29. A method according to claim 25, wherein the compound of formula (I) is applied to said seeds at a dose rate of from about 2 to about 1000 grams per quintal of seed.

30. A method according to claim 29, wherein the application rate is from about 5 to about 800 grams per quintal of seed.

31. A method according to claim 30, wherein the application rate is from about 5 to about 250 grams per quintal of seed.

* * * * *